United States Patent [19]

Babin et al.

[11] Patent Number: 5,310,751
[45] Date of Patent: May 10, 1994

[54] PYRETHRINOID ESTERS OF 1,3,4,5,6,7-HEXAHYDRO-1,3-DIOXO-2H-ISOINDOL-2-YL-METHANOL AND PESTICIDAL COMPOSITIONS THEREOF

[75] Inventors: Didier Babin, Montigny; Marc Benoit, Roquevaire; Jacques Demassey, Montevrain; Jean-Pierre Demoute, Neuilly Plaisance, all of France

[73] Assignee: Roussel Uclaf, France

[21] Appl. No.: 906,405

[22] Filed: Jul. 1, 1992

[30] Foreign Application Priority Data

Jul. 4, 1991 [FR] France .................. 91 08379

[51] Int. Cl.⁵ .................. A61K 31/40; C07D 209/49
[52] U.S. Cl. .................. 514/417; 548/479
[58] Field of Search .................. 548/479; 514/417

[56] References Cited

U.S. PATENT DOCUMENTS

| | | | |
|---|---|---|---|
| 4,833,163 | 5/1989 | Martel et al. | 514/531 |
| 4,849,449 | 7/1989 | Tessier et al. | 514/521 |

FOREIGN PATENT DOCUMENTS

| | | | |
|---|---|---|---|
| 2409261 | 6/1979 | France . | |
| 0041021 | 12/1981 | France . | |
| 1052119 | 12/1966 | United Kingdom . | |
| 1413491 | 11/1975 | United Kingdom | 548/479 |

*Primary Examiner*—Mary C. Lee
*Assistant Examiner*—Jacqueline Haley
*Attorney, Agent, or Firm*—Bierman and Muserlian

[57] ABSTRACT

All possible stereoisomer forms and mixtures thereof of a compound of the formula

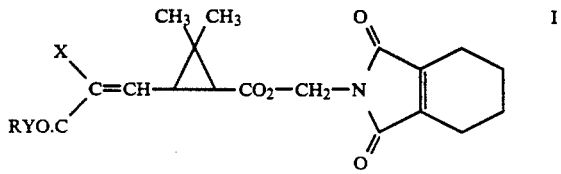

wherein X is halogen, Y is —O— or —S— and R is selected from the group consisting of optionally substituted alkyl, alkenyl and alkynyl of up to 8 carbon atoms, cycloalkyl of 3 to 8 carbon atoms, optionally substituted aryl and aralkyl of up to 14 carbon atoms and optionally substituted heterocyclic having pesticidal properties.

18 Claims, No Drawings

PYRETHRINOID ESTERS OF 1,3,4,5,6,7-HEXAHYDRO-1,3-DIOXO-2H-ISOINDOL-2-YL-METHANOL AND PESTICIDAL COMPOSITIONS THEREOF

OBJECTS OF THE INVENTION

It is an object of the invention to provide the novel compounds of formula I and a process for their preparation.

It is another object of the invention to provide novel pesticidal compositions and a method of combatting pests.

These and other objects and advantages of the invention will become obvious from the following detailed description.

THE INVENTION

The novel compounds of the invention are all possible stereoisomer forms and mixtures thereof of a compound of the formula

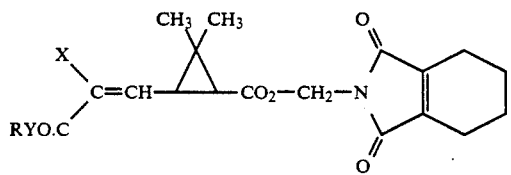

wherein X is halogen, Y is —O— or —S— and R is selected from the group consisting of optionally substituted alkyl, alkenyl and alkynyl of up to 8 carbon atoms, cycloalkyl of 3 to 8 carbon atoms, optionally substituted aryl and aralkyl of up to 14 carbon atoms and optionally substituted heterocyclic.

X is preferably fluorine, chlorine or bromine and examples of R as alkyl are methyl, ethyl, propyl, isopropyl, butyl, sec-butyl, isobutyl, pentyl, hexyl, tert.-butyl, tert-pentyl or neopentyl.

When R is cycloalkyl, it is preferably cyclopropyl, cyclobutyl, cyclopentyl or cyclohexyl or cycloalkylalkyl such as cyclopropylmethyl or cyclopropyl, cyclobutyl, cyclopentyl or cyclohexyl substituted by one or more alkyl whose bond with the —COO— group is situated on any one of its vertices such as 1-methylcyclobutyl, 1-methylcyclopentyl, 1-methylcyclohexyl or 2,2,3,3-tetramethylcyclopropyl.

Examples of R as alkenyl are vinyl or 1,1-dimethylallyl and examples of R as alkynyl are ethynyl and propynyl. Examples of substituted alkyl for R are methyl, ethyl, propyl, isopropyl, butyl, tert.-butyl and isobutyl substituted with at least one functional group selected from the group consisting of halogen, —OR', —SR', —NO$_2$,

—CN, —SO$_3$H, —PO$_4$H$_2$, —COAlk$_1$, —SO$_2$Alk$_2$ and —SO$_3$Alk$_3$, R', R'' and R''' are individually hydrogen or alkyl of 1 to 8 carbon atoms and Alk$_1$, Alk$_2$ and Alk$_3$ are individually alkyl of 1 to 8 carbon atoms.

R may also be alkyl sustituted by aryl such as benzyl or phenethyl optionally substituted by at least one member of the group consisting of —OH, Alk, —OAlk, Alk is alkyl of 1 to 8 carbon atoms, halogen, —CF$_3$, —OCF$_3$, —SCF$_3$ and

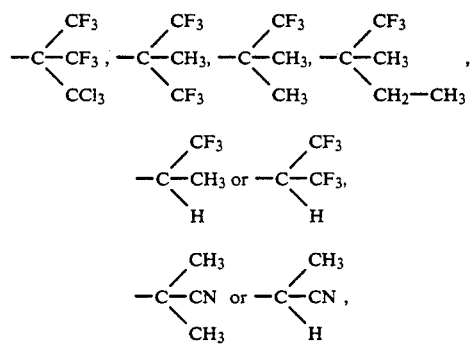

R may also be alkyl substituted on two adjacent carbons by

When R is alkyl substituted by one or more functional groups, preferred examples are —(CH$_2$)$_n$—C(Hal)$_3$ in which n is an integer from 1 to 8 and Hal is halogen, for example —CH$_2$CCl$_3$, —CH$_2$CF$_3$, —CH$_2$—CH$_2$—CCl$_3$ or —CH$_2$—CH$_2$—CF$_3$; —(CH$_2$)$_{n1}$—CH(Hal)$_2$ in which Hal is defined as above and n$_1$ is a number from 0 to 8, for example —CH$_2$—CHCl$_2$, —CH$_2$CHF$_2$ or —CHF$_2$; —(CH$_2$)$_n$Hal in which n and Hal are defined as above, for example —CH$_2$—CH$_2$Cl or —CH$_2$—CH$_2$F; —C—(C(Hal)$_3$)$_3$ in which Hal is defined as above, for example —C(CF$_3$)$_3$ or or —(CH$_2$)$_n$—CN, in which n is defined as previously,

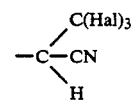

in which Hal is defined as previously, for example

—(CH$_2$)$_n$—OR', in which n is defined as previously and R' is hydrogen or alkyl of 1 to 8 carbon atoms, for example —CH$_2$—OCH$_3$, —CH$_2$—CH$_2$—O—CH$_3$, —CH$_2$—CH$_2$—O—CH$_2$—CH$_3$ or —CH$_2$—CH$_2$—OH,

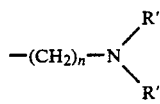

in which n and R' are defined as previously and the two R' can be different from each other, for example

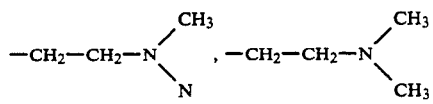

or

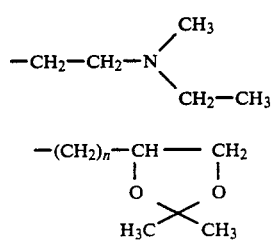

in which n is defined as previously, for example

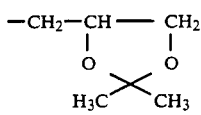

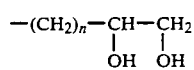

in which n is defined as previously, for example

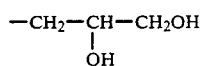

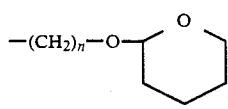

in which n is defined as previously, for example

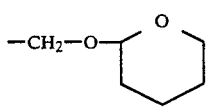

or

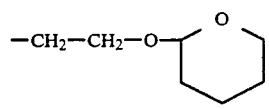

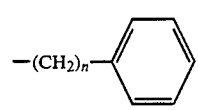

in which n is defined as previously, for example benzyl or phenethyl

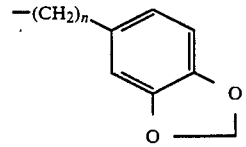

in which n is defined as previously, for example

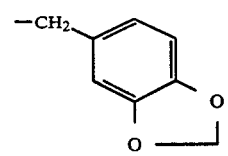

When R is an optionally substituted aryl, it is preferably phenyl or phenyl substituted by one or more OH, OAlk wherein Alk is alkyl of 1 to 8 carbon atoms, or halogen or —$CF_3$, —$OCF_3$ or —$SCF_3$.

When R is a hoterocyclic, it is preferably pyridinyl, furanyl, thiophenyl, oxazolyl or thiazolyl.

Among the preferred compounds of formula I are those wherein the cyclopropane moiety has 1R, cis structure, those wherein the geometry of the vinyl double bond is E, those wherein Y is —O—, those wherein X is fluorine, and those wherein R is alkyl or cycloalkyl of up to 4 carbon atoms, most preferably ethyl or cyclopropyl.

The novel process of the invention for the preparation of the compounds of formula I comprises reacting an acid of the formula

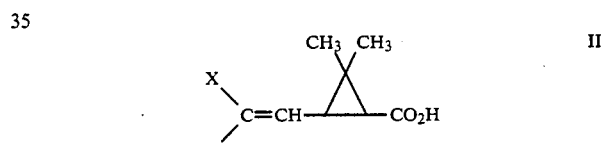

in which X, Y and R are defined as previously, or a functional derivative thereof with an alcohol of the formula

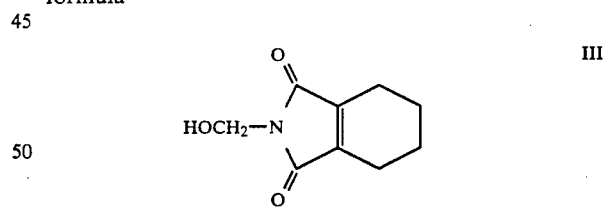

or a functional derivative of this alcohol to obtain the corresponding compound of formula I.

The functional derivative of the acid used is preferably an acid chloride. In a preferred mode, the acid of formula II and the alcohol of formula III are reacted in the presence of dicyclohexylcarbodiimide.

The acids of formula II in which Y is oxygen are known products (EP No. 50,534). The acids of formula II in which Y is sulfur are products known generally which can be prepared by the hydrolysis of known esters described in European Patent No. 0,108,679.

The novel pesticidal compositions of the invention are comprised of a pesticidally effective amount of at least one compound of formula I and an inert carrier. The compositions may be in the form of powders, granules suspensions, emulsions, solutions, aerosol solutions, combustible bands, baits and other known preparations.

The compositions generally contain a liquid and/or a non-ionic, surface-active agent to ensure a uniform dispersion. The vehicle may be a liquid such as water, alcohol, hydrocarbons or other organic solvents, mineral, animal or vegetable oils, powders such as talc, clays, silicates, kieselguhr or a combustible solid.

The compositions are useful for combatting parasites such as for combatting parasites of premises, parasites of vegetation and parasites of warm-blooded animals. Thus the compositions of the invention can be used for combatting insects, nematodes and parasitic acaridae of vegetation and animals.

The compositions can also be used for combatting insects in premises, particularly flies, mosquitoes and cockroaches and can also be used for combatting insects in the agricultural domain such as aphides, larvae of lepidoptera and coleoptera. They are used at doses between 10 g and 300 g of active ingredient per hectare. The compounds of formula I have particularly a very good knock-down power.

From the results of the biological tests hereafter, it can be seen that the products of formula I also possess a remarkable aphicide activity and the compositions can also be used for combatting parasitic acaridae of vegetation and for combatting parasitic nematodes of vegetation.

The compositions can also be used for combatting parasitic acaridae of animals for example ticks and notably ticks of the Boophilus species, those of the Hyalomnia species, those of the Amblyomnia species and those of the Rhipicephalus species, or for combatting all types of mites and notably the sarcoptic, psoroptic and chorioptic mites.

The compositions of the invention are prepared by the usual processes of the agrochemical industry or the veterinary industry or the industry of products intended for animal fodder.

The insecticide compositions contain as active ingredient at least one of the products of formula I and preferably contain 0.005% to 10% by weight of active ingredient. In an advantageous operating method for use in premises, the insecticide compositions of the invention are used in the form of fumigant compositions which can advantageously contain as the non-active part, a combustible insecticide coil, or an incombustible fibrous substrate. In the latter case, the fumigant obtained after incorporation of the active ingredient is placed on a heating apparatus such as an electric vaporizer.

In the case where an insecticide coil is used, the inert support can be, for example, pyrethrum marc compound, Tabu powder (or Machilus Thumbergii leaf powder), pyrethrum stem powder, cedar leaf powder, sawdust (such as pine sawdust), starch and coconut shell powder. The dose of active ingredient can then be, for example, 0.03 to 1% by weight. In the case of an incombustible fibrous support, the dose of active ingredient can be, for example, 0.03 to 95% by weight.

The compositions of the invention for use in premises can also be obtained by preparing a sprayable oil based on the active ingredient the oil soaking the wick of a lamp and then being lit. The concentration of active ingredient incorporated in the oil is preferably 0.03 to 95% by weight.

The acaricide or nematocide compositions contain as active ingredient at least one of the products of formula I defined above.

The insecticide compositions of the invention, as acaricide and nematocide compositions, can optionally have added to them one or more other pesticide agents. The acaricide and nematocide compositions can be presented notably in the form of powder, granules, suspensions, emulsions, solutions.

For acaricide use, wettable powders for foliar spraying containing 1 to 80% of active ingredient or liquids for foliar spraying containing 1 to 500 g/liter of active ingredient are preferably used. Powders for foliar dusting containing 0.05 to 3% of active ingredient can also be used. For nematocide use, liquids for soil treatment containing 300 to 500 g/liter of active ingredient are preferably used. The acaricide and nematicide compositions of the invention are used preferably at doses between 1 and 100 g of active ingredient per hectare.

It can also be noted that the products of the invention can be used as biocides or as growth regulators.

The compositions of the invention may be a mixture of at least one compound of formula I and at least one pyrethrinoid ester selected from the group consisting of esters of allethrolone, of 3,4,5,6-tetrahydrophthalimidomethyl alcohol, of 5-benzyl-3-furyl methyl alcohol, of 3-phenoxybenzyl alcohol and of α-cyano-3-phenoxybenzyl alcohol with chrysanthemic acids, by the esters of 5-benzyl-3-furyl methyl alcohol with 2,2-dimethyl-3-(2-oxo-3-3,4,5,6-tetrahydrothiophenylidenemethyl)-cyclopropanecarboxylic acids, by the esters of 3-phenoxybenzyl alcohol and of α-cyano-3-phenoxybenzyl alcohol with 2,2-dimethyl-3-(2,2-dichlorovinyl)-cyclopropane carboxylic acid, by the esters of α-cyano-3-phenoxybenzyl alcohol with 2,2-dimethyl-3-(2,2-dibromovinyl)-cyclopropane carboxylic acid, by the esters of 3-phenoxybenzyl alcohol with 2-parachlorophenyl-2-isopropyl acetic acid, by the esters of allethrolone, of 3,4,5,6-tetrahydrophthalimidomethyl alcohol, of 5-benzyl-3-furyl methyl alcohol, of 3-phenoxybenzyl alcohol, and of α-cyano-3-phenoxybenzyl alcohol with 2,2-dimethyl-3-(1,2,2,2-tetrahaloethyl)-cyclopropane carboxylic acids, in which "halo" represents a fluorine, chlorine or bromine atom, it being understood that the compounds (I) can exists in all their possible stereoisomer forms, as well as the acid and alcohol copulas of the above pyrethrinoid esters.

The compositions of the invention are in particular useful both for combatting, by the polyvalency of their action, a wide range of parasites, and for demonstrating, in some cases, a synergistic effect.

To enhance the biological activity of the products of the invention, they can have added the standard synergists such as 1-(2,5,8-trioxadodecyl)-2-propyl-4,5-methylenedioxy benzene (or piperonyl butoxide) or N-(2-ethyl-heptyl)-bicyclo-[2,2-1]-5-heptene-2,3-dicarboximide, or piperonyl-bis-2-(2'-n-butoxy-ethoxy)-ethylacetal (or tropital).

The novel method of the invention for combatting parasites comprises contacting the parasites with a parasitically effective amount of at least one compound of formula I. The method is particularly useful for combatting insects.

In the following examples, there are described several preferred embodiments to illustrate the invention. However, it should be understood that the invention is not intended to be limited to the specific embodiments.

EXAMPLE 1

(1,3,4,5,6,7-hexahydro-1,3-dioxo-2H-isoindol-2-yl)-methyl 1R[1α, 3 α,E]-3-[2-fluoro-3-ethoxy-3-oxo-1-propenyl]-2,2-dimethyl cyclopropane carboxylate A solution of 1.3 g of dicyclohexylcarbodiimide and 5 ml of methylene chloride was added at 0° C. to a mixture of 980 mg of (1,3,4,5,6,7-hexahydro-1,3-dioxo-2H-isoindol)-methyl alcohol, 1.47 g of lR[1α, 3α, E]-3-[2-fluoro-3-ethoxy-3-oxo-1-propenyl]-2,2-dimethyl cyclopropanecarboxylic acid, 10 ml of methylene chloride and 70 mg of 4-dimethylamino-pyridine. The reaction mixture was stirred for 16 hours at ambient temperature and filtered. The filtrate was rinsed with methylene chloride and concentrated to dryness to obtain 2.68 g of a product which was chromatographed on silica, eluting with a hexane - ethyl acetate mixture (9-1) to obtain 2.05 g of the desired product with a specific rotation of $[\alpha]_D = +2 \pm 1°$ (c=0.9% in CHCl$_3$).

Using the above procedure the appropriate acids II and the alcohol III were reacted to obtain the following products.

EXAMPLE 2

(1,3,4,5,6,7-hexahydro-1,3-dioxo-2H-isoindol-2-yl)-methyl 1R-(1α, 3α, E]-3-[2-fluoro-3-methoxy-3-oxo-1-propenyl]-2,2-dimethyl cyclopropane carboxylate melting at 97° C. and having a specific rotation $[\alpha]_D = +3\pm1°$ (c=1% in CHCl$_3$).

EXAMPLE 3

(1,3,4,5,6,7-hexahydro-1,3-dioxo-2H-isoindol-2-yl)-methyl [1R-(1α, 3α, E)]-3-[2-fluoro-3-cyclopropyloxy-3-oxo-1-propenyl]-2,2-dimethyl cyclopropanecarboxylate with a specific rotation of $[\alpha]_D = +1°5\pm2°$ (c=0.3% in CHCl$_3$).

EXAMPLE 4

(1,3,4,5,6,7-hexahydro-1,3-dioxo-2H-isoindol-2-yl)-methyl [1R-(1α, 3α, E]-3-[2-fluoro-3-methylthio-3-oxo-1-propenyl]-2,2-dimethyl cyclopropane-carboxylate with a specific rotation of $[\alpha]_D \times -21°\pm2°$ (c×0.6% in CHCl$_3$).

EXAMPLE 5

An emulsifiable concentrate was prepared as a homogeneous mixture of:

| Product of Example 1 | 1.5 g |
| --- | --- |
| Tween 80 | 20.0 g |
| Topanol A | 0.1 g |
| Xylene | 78.4 g |

EXAMPLE 6

A fumigant composition were prepared by mixing homogeneously the following:

| Product of Example 1 | 0.25 g |
| --- | --- |
| Tabu powder | 25.00 g |
| Cedar leaf powder | 40.00 g |
| Pine sawdust | 33.75 g |
| Brilliant green | 0.50 g |
| p-nitrophenol | 0.50 g |

PESTICIDE ACTIVITY

Study of the knock-down effect on the housefly

The test insects were 4-day old female houseflies and the operation was carried out by direct spraying at a concentration of 0.1 g/liter in a Kearns and March chamber using a mixture of acetone (5%) and Isopar 1 (petroleum solvent) as solvent (quantity of solvent used 2 ml per second). 50 insects per treatment were used and checks were carried out every minute for 10 minutes, then after 15 minutes, and the KT50 was determined by the usual methods. The experimental results obtained are summarized in the following table, and they are expressed in relative power relative to bioallethrine.

Product of Example 1 = 12.6
Product of Example 2 = 7.6
Product of Example 3 = 11.3
Product of Example 4 = 5.6

Various modifications of the compounds and method of the invention may be made without departing from the spirit or scope thereof and it is to be understood that the invention is intended to be limited only as defined in the appended claims.

We claim:

1. A compound selected from the group consisting of all possible steroisomer forms and mixtures thereof of a compound of the formula

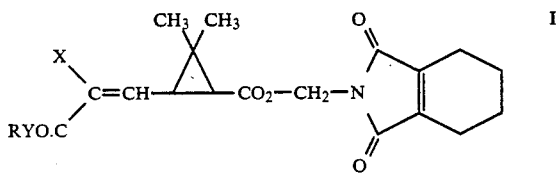

wherein X is fluorine, Y is —O— or —S— and R is alkyl or cycloalkyl of up to 4 carbon atoms.

2. A compound of claim 1 wherein the cyclopropane moiety has 1R cis structure.

3. A compound of claim 1 wherein the double bond geometry is E.

4. A compound of claim 1 wherein Y is —O—.

5. A compound of claim 1 wherein R is ethyl.

6. A compound of claim 1 wherein R is cyclopropyl.

7. A compound of claim 1 selected from the group consisting of (1,3,4,5,6,7-hexahydro-1,3-dioxo-2H-isoindol-2-yl)-methyl 1R-[1α, 3, E]-3-[2-fluoro-3-ethoxy-3-oxo-1-propenyl]-2,2-dimethyl-cyclopropane carboxylate, (1,3,4,5,6,7-hexahydro-1,3-dioxo-2H-isoindol-2-yl)-methyl 1R-[1α, 3α, E]-3-[2-fluoro-3-methoxy-3-oxo-1-propenyl]-2,2-dimethyl cyclopropane carboxylate, (1,3,4,5,6,7-hexahydro-1,3-dioxo-2H-isoindol-2-yl)-methyl [1R-(1α, 3α, E)]-3-[2-fluoro-3-cyclopropyloxy-3-oxo-1-propenyl]-2,2-dimethyl cyclopropane carboxylate and (1,3,4,5,6,7-hexahydro-1,3-dioxo2H-isoindol-2-yl)-methyl [1R-(1α,3α,E)]-3-[2-fluoro -3-methylthio-3-oxo-1-propenyl]-2,2-dimethyl cyclopropane carboxylate.

8. A pesticidal composition comprising a pesticidally effective amount of at least one compound of claim 1 and an inert carrier.

9. An insecticidal composition comprising an insecticidally effective amount of at least one compound of claim 1 and an inert carrier.

10. A composition of claim 9 wherein the active compound is selected from the group con of (1,3,4,5,6,7-hexahydro-1,3-dioxo-2H-isoindol-2-yl) methyl 1R-[1α, 3α, E]-3-[2-fluoro-3-ethoxy-3-oxo-1-propenyl]-2,2-dimethyl-cyclopropane carboxylate, (1,3,4,5,6,7-hexahydro-1,3-dioxo-2H-isoindol-2-yl)-methyl 1R-[1α, 3α, E]-3-[2-fluoro-3-methoxy-3-oxo-1-propenyl]-2,2-dimethyl cyclopropane carboxylate, (1,3,4,5,6,7-hexahydro-1,3-dioxo-2H-isoindol-2-yl)-methyl [1R-(1α, 3α, E)-3-[2-fluoro-3-cyclo-propyloxy-3-oxo-1-propenyl]-2,2-dimethyl cyclopropane carboxylate and (1,3,4,5,6,7-hexahydro-1,3-dioxo-2H-isoindol-2-yl)-methyl [1R-(1α, 3 α, E)]-3-[2-fluoro-3-methylthio-3-oxo-1-propenyl]-2,2-dimethyl cyclopropane carboxylate.

11. A method of combatting pests comprising contacting pests with a pesticidally effective amount of at least one compound of claim 1.

12. A method of combatting insects comprising contacting insects with an insecticidally effective amount of at least one compound of claim 1.

13. The method of claim 12 wherein the cyclopropane moiety has 1R cis structure.

14. The method of claim 12 wherein the double bond geometry is E.

15. The method of claim 12 wherein Y is —O—.

16. The method of claim 12 wherein R is ethyl.

17. The method of claim 12 wherein R is cyclopropyl.

18. The method of claim 12 wherein the active compound is selected from the group consisting of (1,3,4,5,6,7-hexahydro-1,3-dioxo-2H-isoindol2-yl) methyl 1R-[1α, 3α, (E)]-2-[2-fluoro-3-ethoxy-3-oxo1-propenyl]-2,2-dimethyl-cyclopropane carboxylate, (1,3,4,5, 6,7-hexahydro-1,3-dioxo-2H-isoindol-2-yl)-methyl 1R-[1α, 3 α, E]-3-[2-fluoro-3-methoxy-3-oxo-1-propenyl]-2,2-dimethyl cyclopropane carboxylate, (1,3,4,5,6,7-hexahydro-1,3-dioxo-2H-isoindol-2-yl)-methyl [1R-(1α, 3α, E)]-3-[2-fluoro-3-cyclopropyloxy-3-oxo-1-propenyl]-2 2-dimethyl-cyclopropanecarboxylate, (1 3,4,5,6,7-hexahydro-1,3-dioxo-2H-isoindol-2-yl)-methyl [1R-(1α, 3 α, E)]-3-[2-fluoro-3-methylthio-3-oxo-1-propenyl]-2,2-dimethyl cyclopropane carboxylate.

* * * * *